United States Patent
Kiefer et al.

(10) Patent No.: US 7,244,455 B2
(45) Date of Patent: Jul. 17, 2007

(54) CENTER-FILLED CHEWING GUM CONTAINING A DELIVERABLE FORM OF CALCIUM

(75) Inventors: Jesse John Kiefer, Belvidere, NJ (US); Hector Olaya, Parsippany, NJ (US); Carolina Buitron Kellstein, Bridgewater, NJ (US); Blake Henderson Glenn, Oak Ridge, NJ (US)

(73) Assignee: Warner-Lambert Company, Morris Plains, NJ (US)

( * ) Notice: Subject to any disclaimer, the term of this patent is extended or adjusted under 35 U.S.C. 154(b) by 188 days.

(21) Appl. No.: 10/047,967

(22) Filed: Jan. 16, 2002

(65) Prior Publication Data

US 2003/0138518 A1   Jul. 24, 2003

(51) Int. Cl.
*A23G 4/06* (2006.01)
*A23G 4/20* (2006.01)

(52) U.S. Cl. .............................. 426/3; 424/48; 424/440

(58) Field of Classification Search .................. 426/3, 426/5; 424/48, 440
See application file for complete search history.

(56) References Cited

U.S. PATENT DOCUMENTS

| | | | |
|---|---|---|---|
| 4,316,915 A | 2/1982 | Friello et al. |
| 4,352,823 A | 10/1982 | Cherukuri et al. |
| 4,352,825 A | 10/1982 | Cherukuri et al. |
| 4,374,858 A | 2/1983 | Glass et al. |
| 4,513,012 A | 4/1985 | Carroll et al. |
| 4,683,138 A | 7/1987 | Glass et al. |
| 5,670,163 A | 9/1997 | Cuca et al. |

FOREIGN PATENT DOCUMENTS

| | | |
|---|---|---|
| EP | 0 086 856 | 8/1983 |
| EP | 1 151 673 | 11/2001 |
| WO | WO 00/06127 | 2/2000 |
| WO | WO 00/19977 | 4/2000 |
| WO | WO 01/67884 | 9/2001 |

*Primary Examiner*—Arthur L. Corbin
(74) *Attorney, Agent, or Firm*—Watov & Kipnes, P.C.

(57) ABSTRACT

A centerfill chewing gum composition having a shell portion and a centerfill portion, the centerfill portion containing an effective amount of a calcium-containing compound suspended therein.

15 Claims, No Drawings

CENTER-FILLED CHEWING GUM CONTAINING A DELIVERABLE FORM OF CALCIUM

FIELD OF THE INVENTION

The present invention is generally directed to a centerfill chewing gum composition in which a deliverable form of calcium is present in the centerfill. The chewing gum composition delivers calcium to the oral cavity in amounts which can provide up to and exceeding the minimum daily dosage requirements of calcium for an average person through chewing as few as three pieces of gum per day.

BACKGROUND OF THE INVENTION

Calcium-containing compounds such as calcium carbonate have been employed in products which are placed in the oral cavity. For example, Chau et al. (U.S. Pat. No. 5,637,313) discloses a chewable dosage form using calcium carbonate as a bulking agent. Gallopo et al. (U.S. Pat. No. 5,077,051) discloses the sustained release of active agents in the form of bioadhesive microcapsules where calcium carbonate is used as a buffering agent. Cuca et al. (U.S. Pat. Nos. 5,670,163 and 5,858,391) disclose long acting gastrointestinal and esophageal protectants which can include mineral substances such as calcium carbonate.

Calcium is a mineral which requires daily replenishing to sustain healthy bones, teeth and the like. Calcium is not readily stored in the body and therefore must be replenished daily such as by eating foods rich in available calcium. The vitamin and nutraceutical industry has for many years provided supplements for daily intake which include a variety of minerals and vitamins including calcium-containing compounds such as calcium carbonate, calcium citrate and the like.

Ingesting the proper minimum dosage requirement of calcium is largely dependent on the discipline of the individual. In particular, the individual must eat a sufficient amount of calcium-containing foods and/or take calcium-containing supplements. In order to maintain a proper level of available calcium in the body, it is often necessary to eat calcium-containing foods and/or calcium-containing supplements multiple times in a single 24 hour period. This presents problems to many individuals who may not be able to eat calcium-containing foods and/or take calcium-containing supplements as required.

It would therefore be a benefit to provide a convenient vehicle for delivering calcium to an individual which can be easily consumed, is readily available, and can be taken by the individual at any time during the day as needed without having to sit down and eat a meal or resort to capsules or tablets containing calcium.

Chewing gum compositions are used by many individuals because they are readily available, easily transported and provide chewing satisfaction. Chewing gum is a convenient product which does not burden the user or require a break from daily routines.

In recent years, chewing gum compositions have been provided with various additives such as, for example, stain removing agents, antibiotics, and mineral supplements including calcium-containing compounds. For example, International Publication No. WO 98/18339 discloses a chewing gum composition containing bone minerals, calcium triphosphate and/or hydroxyapatite in a gum base. The product is used for supplementing dietary calcium for the prevention of osteoporosis, accelerating development of bones and teeth and the like. German Patent Document No. DE3941490 discloses a chewing gum composition with a core uniformly surrounded by a sugar coating containing soluble minerals including one or more of calcium citrate and calcium chloride. A further example is set forth in Cherukuri et al. (U.S. Pat. No. 4,971,806) which discloses a multi-layer chewing gum composition in which the gum base may include mineral adjuvants such as calcium carbonate, dicalcium phosphate and tricalcium phosphate.

A chewing gum composition containing a liquid or semi-solid center is generally known as a centerfilled chewing gum composition. One such example is disclosed in Ogawa et al. (U.S. Pat. No. 4,157,402) which discloses that additives such as calcium carbonate may be added to the chewing gum base.

Chewing gum compositions present unique problems in delivering agents contained therein. Such compositions typically comprise a water-insoluble gum base which provides the bulk to the gum composition but which invariably traps agents having compatibility with the gum base. Adding additional amounts of an agent to the gum base to compensate for the amount of the agent trapped therein is problematical because the additional amounts of agents often adversely affect the integrity, sensory and/or taste properties of the gum composition.

It would therefore be a significant advance in the art of forming chewing gum compositions for the delivery of calcium to provide a composition which effectively enables the user to readily consume at least a minimum daily requirement of calcium in a routine manner. It would be another significant advance in the art if a chewing gum composition can provide a sufficient amount of calcium per piece so as to provide the minimum daily dosage requirement with no more than about three pieces of the chewing gum composition per day. It would be a further advance in the art to provide a chewing gum composition including a calcium-containing compound which maintains excellent taste and sensory characteristics.

SUMMARY OF THE INVENTION

The present invention is generally directed to a centerfill chewing gum composition in which a deliverable form of calcium is present in the centerfill.

In a particular aspect of the present invention there is provided a centerfill chewing gum composition comprising a chewing gum base and a centerfill comprising an effective amount of a calcium-containing compound suspended in the centerfill. In a preferred form of the invention, the amount of deliverable calcium in the centerfill is sufficient to provide a minimum daily dosage of calcium to an individual upon chewing from three to five pieces of gum per day, most preferably about three pieces of gum per day.

DETAILED DESCRIPTION OF THE INVENTION

The incorporation of a calcium-containing compound into a chewing gum composition requires several considerations. First, calcium-containing compounds can range from essentially water soluble materials such as calcium citrate, calcium lactate, calcium gluconate and the like to essentially sparingly water soluble or non-water soluble materials such as calcium carbonate. Generally, water soluble calcium-containing compounds do not possess a sufficiently high calcium content to readily provide an effective amount of calcium through a chewing gum composition. It is estimated that a chewing gum composition capable of delivering a reasonably good source of calcium per piece would require the delivery of approximately 120 mg of calcium per piece of the chewing gum composition. It will be understood that the amount (120 mg) is an estimate and will vary from individual to individual based on, for example, the size of the individual, the general health of the individual and the particular need for calcium to maintain good health. In order to deliver a sufficient amount of calcium in a chewing gum composition the calcium-containing compound must be present in a sufficient amount so that when released there is enough calcium released into the oral cavity to meet these requirements through chewing a reasonable number of pieces of gum per day (i.e. 3–5 pieces).

Another factor which affects calcium delivery is the amount of the calcium-containing compound which is actually released from the chewing gum composition during the normal chewing cycle. If the calcium-containing compound is bound up in the chewing gum composition and is not released during the normal chewing cycle then the available calcium for delivery to the oral cavity will be insufficient for the desired purpose and will likely not meet the minimum daily requirements of most individuals.

As previously indicated, non-water soluble and sparingly water soluble calcium-containing compounds such as calcium carbonate do not have the disadvantage of water soluble compounds that often make it difficult to deliver enough calcium through chewing a reasonable number of individual pieces of chewing gum. Although, non-water soluble and sparingly water soluble calcium-containing compounds are desirable, the delivery of the same to the oral cavity has been up to the present time difficult to achieve.

One of the major drawbacks of non-water soluble and sparingly water soluble calcium-containing compounds is that they have a high affinity for the gum base and therefore become trapped therein. Therefore, regardless of how much of the calcium-containing compound is provided to the gum base, too little of the calcium-containing compound is released to provide a means of delivering an effective amount of calcium to the individual without detracting from the sensory and taste properties of the chewing gum composition.

In accordance with the present invention, it has been determined that calcium-containing compounds especially non-water soluble and sparingly soluble calcium-containing compounds are preferably provided in the centerfill portion of a centerfill chewing gum composition. In order to make the centerfill portion an effective means of housing the calcium-containing compound and delivering the same to the oral cavity, it is necessary to ensure that the calcium-containing compound is effectively suspended and dispersed throughout the centerfill portion of the chewing gum composition at a viscosity that is consistent with the taste and sensory characteristics of a centerfill chewing gum. In particular, it is desirable to provide a relatively high solids content of the calcium-containing compound in the centerfill portion of the chewing gum composition without affecting the viscosity of the centerfill portion to a point where the taste and/or sensor characteristics of the chewing gum composition are compromised.

It has been observed that non-water soluble and sparingly water soluble calcium-containing compounds (e.g. calcium carbonate) tend to settle out when placed in a liquid environment such as is present in the centerfill portion of a chewing gum composition. This presents problems for a centerfill chewing gum composition because the calcium-containing compound carbonate tends to concentrate in only a relatively small region of the centerfill portion. It is therefore necessary to maintain the calcium compound, such as calcium carbonate, suspended and relatively uniformly dispersed throughout the centerfill portion. That is, the calcium compound should remain evenly distributed throughout the centerfill without settling. The terms "suspended" and "dispersed" are used herein in their common meaning.

Suitable calcium-containing compounds for use in the present invention include in addition to calcium carbonate, for example, calcium oxide, calcium citrate, calcium lactate, calcium gluconate, calcium maleate, calcium phosphate and combinations thereof.

The particle size of the calcium-containing compound is another factor in obtaining the desired distribution of the calcium-containing compound within the center-fill portion. If the particle size of the calcium-containing compound is very low (typically an average particle size of less than about 2 microns), the calcium-containing compound will stay in suspension per se. However, the viscosity of the suspension may exceed desirable limits. Conversely, a relatively large average particle size (typically an average particle size of greater than 14) may provide a desirable viscosity but may also result in the particles of the calcium-containing compound settling out over time as well as imparting a gritty texture to the finished product.

One aspect of the invention provides a suspending or gelling agent which assists in suspending and in maintaining suspension of the calcium-containing compound uniformly throughout the centerfill portion. Such suspending agents include, but are not limited to, carboxymethylcellulose, alginate, pectin, gelatin, starch, and modified starches. The preferred suspending agent is carboxymethylcellulose.

The selection of a suitable molecular weight for the suspending agent is a factor in achieving uniform dispersion of the calcium-containing compound. Generally, the molecular weight of the suspending agent is such that 1% to 2% aqueous solution provides a viscosity in the range of from about 500 to 10,000 cps, preferably from about 2,000 to 6,000 cps. A more preferred molecular weight for carboxymethylcelluose as the preferred suspending agent employed herein is such that the 1% to 2% aqueous solution provides a viscosity of from about 2,500 to 5,500 cps.

It has been observed that an average particle size of from about 0.4 to 17 microns is generally acceptable for the calcium-containing compound. A preferred average particle size range is from about 2 to 8 microns. For calcium carbonate as a preferred calcium-containing compound, an average particle size of from about 3 to 5 microns, most preferably about 4.5 microns is desirable. In one embodiment of the invention, calcium carbonate is the preferred calcium-containing compound and a mixture of particle sizes in the range of from about 0.8 to 14 microns produces an average particle size distribution suitable for use in a centerfill chewing gum composition.

In a second aspect of the invention, it has been found that when an approximate 50/50 mixture (45/55 to 55/45) of a smaller particle size calcium carbonate, e.g., 0.6–1.0 microns, combined with a larger particle size, 14–17 microns, will remain suspended and dispersed in the liquid centerfill, without the use of a suspension agent. In particular it has been found that a mixture of 50% calcium carbonate having a particle size of about 0.8 micron and 50% of calcium carbonate with a particle size of about 15 microns provides a calcium-containing compound which retains stable suspension in a centerfill portion.

The centerfill portion employed in the chewing gum composition of the present invention may be any type of liquid centerfill conventionally used and typically includes a flavoring agent such as one or more essential oils (e.g. peppermint, spearmint, orange, lemon and like), flavoring preparations including all types of fruit flavors and the like. The centerfill portion typically contains a sweetener which may be a sugar selected from disaccharides (e.g. sucrose, lactose, maltose and the like) and polysaccharides (e.g. raffinose, rhamnose, and the like) or sugar substitutes such as polyhydric alcohols (e.g. xylitol, sorbitol, mannitol, and mixtures thereof; as well as maltitol, isomaltitol hydrogenated starch hydrolysates and hydrogenated glucose syrups. Other sugarless sweeteners include free saccharine acid, water soluble salts or saccharin, cyclamate salts, isomalt, dihydrochalcones, glycyrrhizin, L-aspartyl-L-phenylalamine methyl ester, amino based sweeteners, talin, steviosides, and acesulfame salts. Other additives can include gums such as arabic gum, corn syrup and the like in addition to the calcium-containing compound.

The quantity of the centerfill portion of the chewing gum composition may vary over a wide range but will be large enough to include a sufficient amount of the calcium-containing compound to provide the desired release into the oral cavity. The calcium compound may comprise from 20% to 60% of the centerfill portion of the present invention with amounts of 45% to 55% preferred. Typically the amount of the calcium-containing compound will be in an amount sufficient to provide about 120 mg of calcium to the oral cavity. By way of example, if calcium carbonate is selected as the calcium-containing compound approximately 300 milligrams of calcium carbonate will provide the desired amount of calcium and will comprise up to about one-half of the weight (50%) of the centerfill portion.

The centerfill chewing gum composition of the present invention includes a shell or outer portion comprised of any conventional chewing gum formulation. The chewing gum composition may be comprised of a formulation which can be sugar free or may contain sugar.

The chewing gum formulation contains a gum base which generally comprises elastomers, elastomer plasticizers, waxes, fats, oils, emulsifiers, fillers, texturizers and the like prepared in a conventional manner.

The chewing gum formulation further comprises conventional chewing gum ingredients. These ingredients include one or more solvents, plasticizers, fillers, flavoring agents, coloring agents and/or sweetening agents. A general discussion of chewing gum formulation and manufacture may be found in Douglas Fritz, "Chewing Gum Formulation", The Manufacturing Confectioner, Sep., 1988, pp. 128–135, and in E. B. Jackson, Ed. "Sugar Confectionery Manufacture", $2^{nd}$ edition, Blackie Academic & Professional Press, Glasgow UK, (1990), at pages 259–286, incorporated herein by reference.

Elastomers constitute from about 5 to 95% by weight of the base, preferably 10 to 70% by weight and most preferably 15 to 45% by weight. Examples of elastomers includes synthetic elastomers such as polyisobutylene, polybutylene, isobutylene-isoprene co-polymers, styrene-butadiene co-polymers, polyvinylacetate and the like. Elastomers may also include natural elastomers such as natural rubber as well as natural gums such as jelutong, lechi caspi, perillo, massaranduba balata, chicle, gutta hang kang or mixtures thereof. Other elastomers are known to those of ordinary skill in the art.

Elastomer plasticizers modify the finished gum firmness this when used in the gum base. Elastomer plasticizers are typically present in an amount of from about 0 to 75% by weight of the gum base, preferably from about 5 to 45% by weight and most preferably from about 10 to 30% by weight. Examples of elastomer plasticizers include natural rosin esters such as glycerol ester of partially hydrogenated rosin, glycerol ester of tall oil rosin, pentaerythritol esters of partially hydrogenated rosin, methyl and partially hydrogenated methyl esters of rosin, and the like. Synthetic elastomer plasticizers such as terpene resins may also be employed in gum base composition Waxes, fats and oils may be present in an amount up to 30% by weight. Waxes include synthetic and naturally occurring waxes such as polyethylene, bees wax, carnuba, petroleum waxes, microcrystalline waxes. Fats and oils includes animal fats such as lard and tallow, vegetable oils such as soybean and cottonseed oil, hydrogenated and partially hydrogenated vegetable oil, cocoa butter and the like. Waxes, fates and oils aid in the curing of the finished gum and/or help improve the release of flavor and may extend the shelf life of the product.

The shell of the centerfill chewing gum product may also contain conventional coloring agents such as titanium dioxide in amounts up to 2% by weight and fillers which modify the texture of the gum base and aid processing. Examples of such fillers include magnesium and aluminum silicates, clay, alumina, talc, titanium oxide, cellulose polymers, and the like. Fillers are typically present in an amount of from 1 to 60% by weight.

Examples of softeners used in gum base include hydrogenated and partially hydrogenated vegetable oils, cocoa butter, glycerol monostearate, glycerol triacetate, di and tri glycerides, fatty acids such as stearic acid, palmitic acid, oleic acid, linoleic acid, linolenic acid and the like.

The gum base constitutes between 5 and 95% by weight of the chewing gum composition, more typically 10 to 50% by weight, and most preferably 25 to 35% by weight of the chewing gum.

The chewing gum composition may also contain bulk sweeteners including sugars such as sucrose, dextrose, maltose, fructose and the like or sugar alcohols such as sorbitol, mannitol, xylitol, maltitol, isomalt, erythritol and hydrogenated starch hydrolysates and combinations thereof. Bulk sweeteners may be present in amounts up to 90% by weight of the final gum base composition. High intensity sweeteners such as aspartame, acesulfame salts, aliatame saccharin and the like may also be present. These sweeteners may be present in amounts of up to 1% by weight of the final gum base composition.

The chewing gum may contain flavoring agents in addition to the enhanced flavoring compositions in amounts up to 3.5% by weight of the gum base composition. Generally any food additive such as those described in "Chemicals Used In Food Processing", publication 1274, pages 63–258, by the National Academy of Sciences, may be used, the content of which is incorporated herein by reference.

The centerfill chewing gum composition may contain other beneficial ingredients such as vitamins (e.g. vitamins A, B, C, D and E), minerals, mineral salts and botanicals. Minerals include inorganic substances, metals and the like used in the human diet. Minerals include, but are not limited to, zinc, iron and selenium. "Mineral salts" is meant to include the organic and inorganic salts or these minerals and include but are not limited to the gluconate, acetate, chloride and sulfate.

By "botanical" is meant a substance derived from plant source, that is, from roots, leaves, bark or berries of plants, and used in the human diet. Botanicals include, but are not limited to, Echinacea, Siberian Ginseng, Panax Ginseng, Guarana, Ginko Biloba, Kola Nut, Goldenseal, Golo Kola, Schizandra, Elderberry, St. Johns Wort, Valerian and Ephedra. Other examples include B-sitosterol from wheat germ or corn oil, cafestol from green tea, D-limonene from citrus fruits, kabweol from green tea, nomilin from citrus fruits, oltipraz from cruciferous vegetables, sulphoraphane from broccoli, and tangeretin from tangerines. Further examples include extracts from black tea, folic acid, garlic oil, fiber, green tea extract, lemon oil, mace, licorice, menthol, onion oil, orange oil, rosemary extract, and milk thistle extract.

For purposes of the present invention, the centerfill may contain up to 50% by weight of the additional ingredients, preferably up to 40% by weight based on the weight of the centerfill.

The centerfill chewing gum composition of the present invention is typically made by forming a center-fill which may include an optional suspending agent (e.g. carboxy methylcellulose), a flavorant, a sweetener and a calcium-containing compound such as calcium carbonate. The centerfill portion is then injected into the gum base to form a center-fill chewing gum composition. By way of example, a centerfill chewing gum composition may be made by a dual extrusion method wherein the core and the shell are coextruded through an extrusion nozzle and nipped off with a rotary die. A further discussion of the formation of centerfill chewing gum composition can be found in International Publication No. WO 00/06127 incorporated herein by reference.

EXAMPLE 1

Preparation of Sugarless Centerfill Gum Product

A. Sugarless with Suspending Agent

TABLE 1

| Ingredient | Sample 1 |
| --- | --- |
| Gum | |
| Gum base | 23.0 |
| Lecithin | 0.6 |
| Sorbitol | 49.705 |
| Mannitol | 15.00 |
| Glycerin | 9.5 |
| High Intensity sweetener | 0.775 |
| Flavor | 1.42 |
| Total | 100.00 |
| Centerfill | |
| Carboxymethyl cellulose* | 48.9503 |
| Flavor | 0.135 |
| High Intensity Sweetener | 0.025 |
| Calcium Carbonate** | 50.00 |
| Totals | 100.00 |

*Comprised of 50.0% glycerin, 49.25% sorbitol solution and 0.75% carboxymethylcellulose having a molecular weight sufficient to provide a 2% aqueous solution with a viscosity between 2,500 to 5,000 cps.
**A composition containing 98–100% calcium carbonate obtained from Speciality Minerals Inc. of Adam Massachusetts under the trade name Calessence having an average particle size of 4.5 microns.

Sample 1 shown in Table 1 was prepared in a conventional manner. The gum shell is made by conventional blending of the ingredients with the gum base.

The centerfill portion was formed by cooking the ingredients until the resulting cooked centerfill had approximately 85% solids by weight. The product was formed by coextruding the shell mixture and centerfill mixture forming a rope having the centerfill within a tube formed from the shell mixture. The rope was fed into a rotary forming unit to firm individual pieces of the centerfill chewing gum composition of the present invention.

The final gum composition produced pieces of a chewing gum composition weighing about 3.8 g with a centerfill portion comprising about 16% by weight of the gum composition. The centerfill portion contained 304 mg of calcium carbonate providing 121.6 mg of available calcium per piece.

B. Sugarless with No Suspending Agent

TABLE 2

| Ingredient | Sample 2 |
| --- | --- |
| Gum | |
| Gum base | 23.0 |
| Lecithin | 0.6 |
| Sorbitol | 49.705 |
| Mannitol | 15.00 |
| Glycerin | 9.5 |
| High Intensity sweetener | 0.775 |
| Flavor | 1.42 |
| Total | 100.00 |
| Centerfill | |
| Glycerin | 48.9502 |
| Flavor | 1.024 |
| High Intensity Sweetener | 0.025 |
| Calcium Carbonate* | 50.00 |
| Totals | 100.00 |

*A composition containing 98–100% calcium carbonate obtained from Speciality Minerals Inc. of Adam Massachusetts under the trade name Calessence. 50% of the calcium carbonate had an average particle size of 0.8 micron and 50% had an average particle size of 15 microns.

Sample 2 shown in Table 2 was prepared as in the same manner as Sample 1 except carboxymethylcellulose was omitted from the centerfill.

The final gum composition produced pieces of a chewing gum composition weighing about 3.8 g with a centerfill portion comprising about 16% by weight of the gum composition. The centerfill portion contained 304 mg of calcium carbonate providing 121.6 mg of available calcium per piece.

EXAMPLE 2

Preparation of Sugared Centerfill Gum Product

TABLE 3

| Ingredient | Sample 3 |
| --- | --- |
| Gum | |
| Gum base | 21.5 |
| Corn Syrup | 17.5 |
| Lecithin | 0.3 |
| Acetylated Monoglycerides | 0.15 |
| Glycerin | 1.0 |
| Sugar | 58.8048 |
| Flavor | 0.7452 |
| Total | 100.00 |

TABLE 3-continued

| Ingredient | Sample 3 |
|---|---|
| Centerfill | |
| Master Batch* | 44.1064 |
| Glycerin | 4.8991 |
| Flavor | 0.9848 |
| Calcium Carbonate** | 50.00 |
| Totals | 100.00 |

*Comprised of 44.465% corn syrup, 5.3265% sugar, 44.465% high fructose corn syrup and 5.7434% water.
**A composition containing 98–100% calcium carbonate obtained from Speciality Minerals Inc. of Adam Massachusetts under the trade name Calessence comprising the same mixture as used in Example 2.

A. Sugar with no Suspending Agent

Sample 3 shown in Table 3 was prepared as in the same manner as Sample 1 described in Example 1 except that carboxymethyl cellulose was omitted from the centerfill.

The final gum composition produced pieces of a chewing gum composition weighing about 3.8 g with a centerfill portion comprising about 16% by weight of the gum composition. The centerfill portion contained 304 mg of calcium carbonate providing 121.6 mg of available calcium per piece.

What is claimed is:

1. A centerfilled chewing gum composition comprising a shell portion and a centerfill portion, said centerfill portion having no gum base and comprising calcium carbonate having an average particle size of from about 3 to 5 microns suspended in the centerfill portion and being uniformly dispersed therein without settling, and being present in an effective amount sufficient to provide at least the minimum daily nutritional amount of calcium to a user by chewing 3 to 5 pieces of the chewing gum composition per day.

2. The chewing gum composition of claim 1 wherein the centerfill further comprises a suspending agent.

3. The chewing gum composition of claim 2 wherein the suspending agent is selected from the group consisting of alginate, pectin, gelatin, starch, modified starch, and carboxymethylcellulose.

4. The chewing gum composition of claim 2 wherein the suspending agent has a molecular weight such that a 1% to 2% aqueous solution of the suspending agent imparts a viscosity of from about 500 to 10,000 cps to the centerfill portion.

5. The chewing gum composition of claim 4 wherein the viscosity is from about 2,000 to 6,000 cps.

6. The chewing gum composition of claim 5 wherein the viscosity is from about 2,500 to 5,500 cps.

7. The chewing gum composition of claim 1 wherein the centerfill portion further comprises at least one ingredient selected from the group consisting of vitamins, minerals, mineral salts and botanicals.

8. A method of delivering an effective amount of calcium to the oral cavity of a human being comprising chewing 3 to 5 pieces of the chewing gum composition of claim 1.

9. A centerfilled chewing gum composition comprising a shell portion and a centerfill portion, said centerfill portion having no gum base and comprising a suspending agent and calcium carbonate, wherein 50% of the calcium carbonate has a particle size of about 0.8 micron and 50% has a particle size of about 15 microns, suspended in the centerfill portion and being uniformly dispersed therein without settling, and being present in an effective amount sufficient to provide at least the minimum daily nutritional amount of calcium to a user by chewing 3 to 5 pieces of the chewing gum composition per day.

10. The chewing gum composition of claim 9 wherein the suspending agent is selected from the group consisting of alginate, pectin, gelatin, starch, modified starch, and carboxymethylcellulose.

11. The chewing gum composition of claim 9 wherein the suspending agent has a molecular weight such that a 1% to 2% aqueous solution of the suspending agent imparts a viscosity of from about 500 to 10,000 cps to the centerfill portion.

12. The chewing gum composition of claim 11 wherein the viscosity is from about 2,000 to 6,000 cps.

13. The chewing gum composition of claim 12 wherein the viscosity is from about 2,500 to 5,500 cps.

14. The chewing gum composition of claim 9 wherein the centerfill portion further comprises at least one ingredient selected from the group consisting of vitamins, minerals, mineral salts and botanicals.

15. A method of delivering an effective amount of calcium to the oral cavity of a human being comprising chewing 3 to 5 pieces of the chewing gum composition of claim 9.

* * * * *